United States Patent [19]

Terada et al.

[11] Patent Number: 4,734,284

[45] Date of Patent: Mar. 29, 1988

[54] ETOPOSIDE PREPARATIONS

[75] Inventors: Takashi Terada, Yono; Hideyuki Ishimado, Urawa; Masaru Suzuki, Tokyo; Minoru Nakada; Gen'iti Idzu, both of Yono, all of Japan

[73] Assignee: Nippon Kayaku Kabushiki Kaisha, Tokyo, Japan

[21] Appl. No.: 823,362

[22] Filed: Jan. 28, 1986

[30] Foreign Application Priority Data

Feb. 19, 1985 [JP] Japan ................................ 60-31203

[51] Int. Cl.$^4$ ................................................ A61K 9/48
[52] U.S. Cl. ...................................... 424/455; 424/456
[58] Field of Search .............................. 424/455, 456

[56] References Cited

U.S. PATENT DOCUMENTS 4,609,640  9/1986  Morishita et al. ................ 514/12
4,609,644  9/1986  Nemes ................................ 514/27

FOREIGN PATENT DOCUMENTS 0161915  11/1985  European Pat. Off. .
1421144  1/1976  United Kingdom .
2155789  10/1985  United Kingdom .

OTHER PUBLICATIONS

Rote Liste, 85 046 B (1981).
Falkson et al., "A Clinical Trial of the Oral Form of 4'-Demethyl-Epipodophyllotoxin-D Ethylidene Gucoside (NSC 141540) VP 16-213," *Cancer*, vol. 35, pp. 1141-1144 (1975).
Nissen et al., "Phase I Clinical Trial of an Oral Solution of VP-16-213," Cancer Treatment Reports, vol. 60, pp. 943-945 (1976).

*Primary Examiner*—Thurman K. Page
*Assistant Examiner*—Leon R. Horne
*Attorney, Agent, or Firm*—Banner, Birch, McKie and Beckett

[57] ABSTRACT

This invention relates to etoposide solution preparations, which exhibit excellent absorbability in vivo, comprising a container and, enclosed therein, an etoposide solution composition containing etoposide and a water-soluble cellulose derivative or polyvinylpyrrolidone.

12 Claims, No Drawings

ETOPOSIDE PREPARATIONS

BACKGROUND OF THE INVENTION

1. Field of the Invention

This invention relates to pharmaceutical preparations of etoposide, i.e. 4'-demethylepipodophillotoxin-9-(4,6-O-ethylidene-β-D-glucopyranoside) which is believed to be a promising antitumoral agent.

2. Description of the Prior Art

Etoposide is a drug difficultly soluble in water. As solutions, there has been known an injection prepared by dissolving 100 mg of the etoposide in a mixture of 150 mg of benzyl alcohol and 3,250 mg of polyethylene glycol 300, and filling the resulting solution in an ampul of 5 ml in volume (Rote List, 85046 B, 1981).

Because of its bulkiness, however, the etoposide solution is difficultly made into an encapsulated preparation containing the same amount of the drug as that of the injection. To overcome the difficulty, the present inventors had attempted to reduce the amount of the solvent. It was found, however, that the preparation with reduced amount of solvent presents a problem of insufficient absorbability when it is orally administered to a living body. The reason for this is presumably such that upon being added to water this preparation soon separates out etoposide crystals and the same phenomenon would take place in the living body, precipitating the difficultly absorbable crystals.

SUMMARY OF THE INVENTION

Under the circumstances, the present inventors made an extensive study and, as a result, found that an etoposide solution composition containing (1) etoposide and (2) a water-soluble cellulose ether derivative or polyvinylphrrolidone showed a reduced tendecy to separate out crystals when added into water and an improved absorbability when orally administered to a living body. The present invention has been accomplished based on the above finding.

According to this invention there is provided an etoposide solution preparation comprising a container and, enclosed therein, an etoposide solution composition containing etoposide and a water-soluble cellulose ether derivative or polyvinylpyrrolidone.

DETEAILED DESCRIPTION OF THE INVENTION

The invention is described in detail hereunder.

According to this invention, use may be made of any of the solvents which are capable of dissolving etoposide, are pharmacologically acceptable, and are liquid or semisolid at ordinary temperatures. Preferable ones include lower alkyl alcohols such as ethyl alcohol; glycerol; glycols such as propylene glycol; and polyalkylene glycols such as polyethylene glycols 300 and 400. Particularly preferred are polyethylene glycohols having an average molecular weight of 200 to 600. These solvents are used in an amount of generally 5 to 50, preferably 8 to 20, parts by weight for 1 part by weight of etoposide. The solvents are used each alone or in mixtures of two or more. When, for example, a mixture of polyethylene glycol and glycerol is used, the ratio of the former to the latter is about 1000:10–200, preferably about 1000:20–50, by weight.

As examples of water-soluble cellulose ether derivative advantageously used in this invention, mention may be made of cellulose ethers derived by substituting the hydroxyl group(s) of cellulose with a hydroxyalkoxy group and/or a loweralkoxy group, such as hydroxy(loweralkyl ethers of cellulose, e.g. hydroxypropylcellulose; cellulose ethers having a hydroxy(lower)alkyl ether linkage and a loweralkyl ether linkage in one cellulose molecule, e.g. (hydroxypropyl)(methyl)cellulose; and lower alkyl ethers, e.g. methylcellulose. The viscosity (at 20° C.) of a 2% aqueous solution of cellulsoe ethers is generally 2 to 8,000, preferably 3 to 1,500 cps.

The molecular weight of polyvinylpyrrolidone is subjected to no special restriction. Both the polymers of 40,000 and 700,000 in molecular weight can be used without discrimination. However, generally those of 10,000 to 1,000,000, preferably 20,000 to 100,000, in molecular weight is used. The cellulose ehter derivatives or polyvinylpyrrolidones are used each alone or in mixtures of two or more. The amount used of these additives is preferably 0.001 to 0.5, most preferably 0.005 to 0.2, part by weight for 1 part by weight of etoposide. There is no difference in the effectiveness of the additive whether it is used in the form of solution or suspension.

The etoposide content of the present etoposide solution composition is 1 to 16%, preferably 5 to 11%, by weight; the cellulose derivative or polyvinylpyrrolidone content is 0.002 to 10, preferably 0.01 to 3%, by weight. The etoposide solution composition is prepared by dissolving etoposide in a solvent and adding to the resulting solution a water-soluble cellulose ether derivative or polyvinylpyrrolidone. In preparing the solution composition, it is useful for the stabilization of etoposide to add 0.01 to 0.2, preferably 0.03 to 0.1, part by weight of an organic acid such as citric acid, tartaric acid, malic acid, succinic acid, or fumaric acid to 1 part by weight of etoposide. An example of the preferable solution compositions in this case comprises 4–10% of etoposide, 0.1 to 1% of citric acid, 1 to 5% of glyceral, 94.8 to 82% of polyethylene glycol, and 0.1 to 1% of hydroxypropylcellulose, all percentages being by weight. Otehr additives such as stabilizers, flavoring agents, and aromatizing agents can also be added.

The pharmaceutical preparations of this invention are obtained by filling the above-mentioned etoposide solution composition in containers such as glass vials or capsule shells. It is preferable to fill the composition in hard gelatin capsule shells or in soft gelatin capsule shells by the plate process or by means of a capsule filler of the rotary die type at room temperature. Soft gelatin capsules are preferred particularly when the solution composition has a high fluidity, as in the case of citric acid-containing composition described above as the example.

The difficult precipitation of crystals from the present preparations in contact with water and the excellent absorbability of the present composition are demonstrated below with reference to Experimental Examples.

(1) Experiment on precipitation of crystals

1. Sample: Samples were prepared by dissolving 1 part of etoposide in a mixture of 12 parts of polyethylene glycol 400 and 0.3 part of glycerol and adding to the resulting solution the additives shown in Table 1. The composition containing no additive was used as control.

TABLE 1

| Sample No. | Additive | Amount added to 1 part of etoposide |
| --- | --- | --- |
| 1 | Hydroxypropylcellulose (3-6 cps) | 0.005 |
| 2 | " | 0.01 |
| 3 | " | 0.05 |
| 4 | " | 0.2 |
| 5 | (Hydroxypropyl) (methyl)cellulose (6 cps) | 0.05 |
| 6 | Methylcellulose (400 cps) | 0.05 |
| 7 | Polyvinylpyrrolidone (M.W. 40,000) | 0.05 |
| 8 | " | 0.20 |

2. Testing method:

Dissolution tester: that described in Parmacopeia of Japan, 10th Ed.

Testing liquid: Distilled water (250 ml) at 37° C.

Agitation: Paddle stirrer at 50 r.p.m.

Thirty minutes after the addition of 5 ml of the sample solution into the testing liquid, a portion of the latter was filtered through a membrane filter, then diluted 10-fold with distilled water, and the absorbance at 282 nm was determined. Also, the time of first appearance of crystals was visually observed.

3. Results: The results of test were as shown in Table 2.

TABLE 2

| Sample No. | Absorbance* (282 nm) | Time elapsed before Crystallization |
| --- | --- | --- |
| 1 | 1.192 | No crystallization* |
| 2 | 1.120 | " |
| 3 | 1.109 | " |
| 4 | 1.274 | " |
| 5 | 1.154 | " |
| 6 | 1.135 | " |
| 7 | 1.135 | 12 min. (slight crystallization) |
| 8 | 0.935 | No crystallization |
| Control 1 | 0.147 | 1 min. |

*Observation after 30 minutes from the beginning of test.

As is apparent from Table 2, after 30 minutes from the beginning of test, the solution composition of this invention showed a high absorbance and substantially no precipitation of crystals, whereas the control sample showed a very low absorbance and a large amount of crystalline precipitated.

(2) Test for drug concentration in blood

1. Sample: Each 1,300 mg of the sample solutions No. 2 and No. 3 and the control sample used in the crystallization experiment was filled in a soft gelatin capsule.

2. Testing method: Each sample capsule was peroraly administered to a male beagle and the change with time in etoposide content of the blood was determined over a period of 150 minutes. From the curve of etoposide content of the blood, the total concentration of etoposide over a period of 150 minutes was determined and the ratio of total etoposide concentration to that determined for the control was calculated by assuming the latter to be 100.

3. Results: The results obtained were as shown in Table 3.

TABLE 3

| Sample No. | Ratio |
| --- | --- |
| 2 | 200 |
| 3 | 223 |
| Control | 100 |

As is apparent from Table 3, the solution preparation of this invention showed more than twice as much absorption of etoposide compared with the control preparation. The preparation of this invention, therefore, exhibits advantages of reduced crystallization of etoposide in water and improved absorbability of etoposide. A further advantage is the increased and sustained concentration of etoposide in blood of the living body. A still further advantage is the reduction of solvent volume to about one third of that in the case of conventional solution preparation, such a volume reduction being the prerequisite for the production of capsules.

The invention is illustrated in detail hereunder with reference to Examples, in which "parts" are parts by weight.

EXAMPLE 1

Into a mixed solvent of 108 parts of polyethylene glycol 400 and 10 parts of glycerol, was dissolved 10 parts of etoposide followed by 2 parts of polyvinylpyrrolidone to obtain a filling solution. Capsules each containing 50 mg of etoposide were prepared by filling 650 mg of the filling solution in No. 0 hard gelatin capsule shells by means of a capsule filling apparatus provided with a liquid filling unit.

EXAMPLE 2

A filling solution was prepared by dissolving 100 parts of etoposide in 1,100 parts of polyethylene glycol 300 and adding to the resulting solution 1 part of hydroxypropylcellulose. Soft capsules each containing 100 mg of etoposide were prepared by filling 1,300 mg of the filling solution in soft gelatin capsule shells by means of a rotary die process machine and drying the filled capsules.

EXAMPLE 3

A filling solution was prepared by dissolving 100 parts of etoposide in a mixture of 1,100 parts of polyethylene glycol 400 and 30 parts of glycerol and adding to the resulting solution 5 parts of (hydroxypropyl)(methyl)cellulose. Soft capsules each containing 100 mg of etoposide were obtained by filling 1,235 mg of the filling solution in each gelatin capsule by the plate process and drying the filled capsules.

EXAMPLE 4

A solution for oral administration of the following composition was prepared:

|  | Parts |
| --- | --- |
| Etoposide | 100 |
| Polyethylene glycol 400 | 1,770 |
| Polyvinylpyrrolidone K30 | 20 |
| Citric acid | 5 |
| Glycerol | 100 |
| Orange flavor | 5 |

The uniform solution (2.5 g) was filled in a glass vial to obtain a solution medicine.

EXAMPLE 5

Into a mixture of 1,100 parts of polyethylene glycol 300 and 30 parts of glycerol, was dissolved 100 parts of etoposide followed by 5 parts of methylcellulose to prepare a filling solution for soft geratin capsules. In a similar manner to that in Example 3, soft capsules each containing 100 mg of etoposide were obtained.

EXAMPLE 6

Into a mixture of 1,000 parts of polyethylene glycol 300 and 100 parts of glycerol, were dissolved 8 parts of citric acid and 100 parts of etoposide followed by 10 parts of hydroxypropylcellulose. The resulting filling solution was filled in soft gelatin capsule shells by means of a rotary die process machine and dried to reduce the water content of shells to about 8 to about 15% to obtain soft capsules each containing 100 mg of etoposide.

EXAMPLE 7

A filling solution was prepared by dissolving 100 parts of etoposide in a mixture of 1,080 parts of polyethylene glycol 400 and 100 parts of glycerol and adding to the resulting solution 2 parts of hydroxypropylcellulose. Soft capsule suppositories, each 1,600 mg in gross weight, were prepared by filling 1,182 mg of the filling solution in each soft gelatin capsule by means of a rotary die process machine of Leiner and Sons Co.

EXAMPLE 8

A filling solution was prepared by dissolving 5 parts of citric acid and 100 parts of etoposide in a mixture of 1,100 parts of polyethylene glycol 400 and 30 parts of glycerol and adding to the resulting solution 5 parts of hydroxypropylcellulose. Soft capsules, each containing 100 mg of etoposide, were prepared by filling 1,240 mg of the above solution in each gelatin capsule by the plate process.

What is claimed is:

1. An etoposide preparation comprising a vial or capsule and, enclosed therein, an etoposide solution composition containing etoposide and a water-soluble cellulose ether derivative or polyvinylpyrrolidone.

2. A preparation according to claim 1, wherein the water-soluble cellulose ether derivative is one member selected from the group consisting of (a) hydroxy(lower)alkyl ethers of cellulose, (b) cellulose ethers having both the hydroxy(lower)alkyl ether linkage and the lower alkyl ether linkage in one molecule, and (c) lower alkyl ethers of cellulose and has a viscosity of 2 to 8,000 cps (2% aqueous solution at 20° C.).

3. A preparation according to claim 1, wherein the proportion of the cellulose ether derivative or polyvinylpyrrolidone is 0.001–0.5 part by weight to 1 part by weight of etoposide.

4. A preparation according to claim 1, wherein the etoposide solution composition has an etoposide content of 1 to 16% by weight and a cellulose ether derivative or polyvinylpyrrolidone content of 0.002 to 10% by weight.

5. A preparation according to claim 1, whrein the solvent in the etoposide solution composition is a lower alkyl alcohol, a glycol, or a polyalkylene glycol.

6. A preparation according to claim 5, wherein the proportion of the solvent is 5 to 50 parts by weight for 1 part by weight of the etoposide.

7. A preparation according to claim 5, wherein the solvent is ethanol, glycerol, propylene glycol, or polyethylene glycol.

8. A preparation according to claim 5, wherein the solvent is a mixed solvent comprisng a polyethylene glycol of 200 to 600 in average molecular weight and glycerol.

9. A preparation according to claim 8, wherein the ratio of polyethylene glycol to glycerol is 1,000:10–200.

10. A preparation according to claim 1, wherein the etoposide solution composition contains 0.01 to 0.2 part by weight of an organic acid for 1 part by weight of etoposide.

11. A preparation according to claim 10, wherein the organic acid is citric acid, tartaric acid, malic acid, succinic acid, or fumaric acid.

12. A soft gelatin capsule filled with an etoposide solution composition comprising 4–10% (W/W) of etoposide, 0.1–1% (W/W) of citric acid, 1–5% (W/W) of glycerol, 94.8–82% (W/W) of polyethylene glycol, and 0.1–1% (W/W) of hydroxypropylcellulose.

* * * * *